United States Patent [19]

Byers et al.

[11] Patent Number: 5,141,923

[45] Date of Patent: Aug. 25, 1992

[54] METHODS FOR THE TREATMENT OF RETROVIRAL INFECTIONS

[75] Inventors: Vera K. Byers; Alan S. Levin, both of San Francisco, Calif.

[73] Assignee: Immunology, Inc., a California corporation, San Francisco, Calif.

[21] Appl. No.: 635,846

[22] Filed: Dec. 31, 1990

[51] Int. Cl.$^5$ .............................................. A61K 37/02
[52] U.S. Cl. .......................................... 514/12; 514/2; 424/195.1; 530/370
[58] Field of Search .................... 514/12, 2; 424/195.1; 530/370

[56] References Cited

U.S. PATENT DOCUMENTS

| | | | |
|---|---|---|---|
| 4,795,739 | 1/1989 | Lifson et al. | 514/8 |
| 4,869,903 | 9/1989 | Lifson et al. | 424/195.1 |
| 4,937,074 | 6/1990 | Venkateswaran et al. | 424/195.1 |

Primary Examiner—Merrell C. Cashion, Jr.
Assistant Examiner—Choon P. Koh
Attorney, Agent, or Firm—Stephen L. Hurst

[57] ABSTRACT

The present invention provides novel methods for the treatment of retroviral infection, particularly HIV disease. According to the present invention, human HIV infected hosts were selected who had been on a stable dose of an anti-retroviral agent, such as zidovudine, for up to two years prior to administration of the ribosomal inhibiting protein trichosanthin, and who had failed anti-retroviral therapy, as manifest by decrease in CD4+ cells on at least two serial measurements, or loss of over 50 CD4+ cells/mm$^3$/year. These patients remained on the same dose of anti-retroviral agent (AZT or ddI) and received trichosanthin, 1.2 mg weekly, then monthly. A significant number of patients demonstrated improved CD4+ cell counts following administration of trichosanthin as compared to CD4+ cell counts prior to adminstration of the drug.

9 Claims, No Drawings

METHODS FOR THE TREATMENT OF RETROVIRAL INFECTIONS

BACKGROUND OF THE INVENTION

Field of the Invention

This invention relates generally to the field of the treatment of retroviral infections and, more particularly, to the chemotherapeutic treatment of human immunodeficiency virus (HIV) infection and associated disease, including acquired immune deficiency syndrome (AIDS).

Retroviral agents have been implicated in a number of diseases, including cancer, autoimmune disease and AIDS. Human immunodeficiency virus infection causes chronic progressive depletion of CD4+ T lymphocytes (CD4+ cells) and infection of macrophages, resulting in acquired immune deficiency syndrome. Currently zidovudine (AZT), an analogue of thymidine, is the primary anti-viral drug used in the treatment of HIV infection, although two other agents with a similar mechanism of action, dideoxyinosine (ddI) and dideoxycytosine (ddC), are also in clinical trials. Colley, T. P. et al., *New Engl. J. Med.* (1990)322:1340-45; Fischl, M. A., et al., *New Engl. J. Med.* (1987)317:185-91. These agents are effective in inhibiting viral replication, and can stabilize the CD4+ cell levels, but they are unable to eliminate one of the major viral reservoirs, HIV infected macrophages. Gartner, S., et al., *Science* (1986)233:215-19. Severe toxicity, particularly involving HIV host bone marrow is associated with higher doses of zidovudine treatment, and the beneficial effects of the drug in AIDS patients diminishes after prolonged therapy; HIV strains resistant to zidovudine have been observed in treated patients. These findings have prompted the search for alternative drugs for the treatment of HIV infection, particularly agents with a different mechanism of action.

Trichosanthin, derived from the root tuber of *Trichosanthes kirilowii* belongs to a class of proteins including ricin, momorcharins, and trichokirin, which inhibit ribosome synthesis (ribosomal inhibiting proteins or RIPs) and are cytotoxic for a range of mammalian cells. Kubota, S., et al., *Int. J. Peptide Protein Res.* (1987)30:646-51; Zhang, X. and Wang, J., *Nature* (1986)321:477-78; Casellas, P., et al., *Eur. J. Biochem.* (1988)176:581-88. It is presumed that the mechanism of action involves interaction of the protein with 20S ribosomes, and inhibition of protein synthesis. Theoretically, a single trichosanthin molecule reaching the target site is sufficient to cause cell death. Pharmaceutical grade trichosanthin has been used for many years in China as an abortifacient, and anti-cancer agent for choriocarcinoma. Yeung, H. W., et al., *Int. J. Peptide Protein Res.* (1988)31:265-68. It was recently reported to inhibit HIV replication in cultured T lymphoblastoid cells and to be specifically cytotoxic for infected monocyte/macrophages. McGrath, M. S., et al., *Proc. Natl. Acad. Sci. USA* (1989)86:2844-48. These properties have led to its evaluation for the treatment of HIV infected patients.

Two phase I dose escalation studies using this agent in HIV infected patients have recently been reported. In the first, trichosanthin was obtained from China, and 51 patients with advanced HIV disease were removed from all other drugs and given three weekly doses of trichosanthin at doses ranging from 10 to 30 $\mu$g/kg. Dose related side effects were very similar to those seen with other members of this class of compounds, and included reversible hypoalbuminemia. Maximum tolerated dose was 30 $\mu$g/kg/dose, and was defined by severe reversible myalgia. A non-dose related side effect was mental status change presenting as reversible dementia, which could progress to coma. This was associated with CD4+ cell levels less than 100/mm$^3$. Byers, V. S., et al., *AIDS* (1990)4:1189-96. The second study utilized trichosanthin manufactured in the United States, and treated patients at doses of 5-36 $\mu$g/kg as a single injection. Kahn, J. A., et al., *AIDS* (1990)4:1197-1204. Side effects were quite similar between the two studies, and no evidence of bone marrow toxicity was noted, suggesting that combination therapy with zidovudine and trichosanthin would be well tolerated. In those patients with CD4+ cells over 100/mm$^3$, who received three doses of drug, a significant increase in CD4+ cell levels was noted. Byers, V. S., et al., *AIDS* (1990)4:1189-96. The disclosures of all references cited herein are hereby incorporated by reference.

SUMMARY OF THE INVENTION

The present invention provides novel methods for the treatment of retroviral infection, particularly HIV disease. According to the present invention, human HIV infected hosts were selected who had been on a stable dose of an anti-retroviral agent, such as zidovudine, for up to two years prior to administration of the ribosomal inhibiting protein trichosanthin, and who had failed anti-retroviral therapy, as manifest by decrease in CD4+ cells on at least two serial measurements, or loss of over 50 CD4+ cells/mm$^3$/year. These patients remained on the same dose of anti-retroviral agent (AZT or ddi) and received trichosanthin, 1.2 mg weekly, then monthly. A significant number of patients demonstrated improved CD4+ cell counts following administration of trichosanthin as compared to CD4+ cell counts prior to administration of the drug.

DETAILED DESCRIPTION OF THE PREFERRED EMBODIMENTS

The present invention provides novel methods for the chemotherapeutic treatment of human immunodeficiency virus (HIV) infection and associated disease, including acquired immune deficiency syndrome (AIDS).

According to the present invention, retroviral infections are treated by a combination of anti-retroviral agents and ribosomal inhibiting proteins in doses sufficient to diminish the effects of such infection. Retroviral infections are implicated in a number of diseases, including but not limited to cancer, autoimmune disease, and acquired immune deficiency syndrome. Human immunodeficiency virus infection is of particular interest according to the present invention.

A variety of anti-retroviral agents are known in the art. Most of these inhibit the activity of retroviral reverse transcriptase and include zidovudine (AZT), an analogue of thymidine, dideoxyinosine (ddI), and dideoxycytosine (ddC). Zidovudine is the primary antiviral drug used in the treatment of HIV infection. Anti-retroviral agents are generally efficacious in a dose ranging from about 50 mg/day to about 1000 mg/day, more particularly from about 100 mg/day to about 500 mg/day, and, in the case of zidovudine, specifically about 300 mg/day to about 500 mg/day. These agents are generally administered in oral formulations.

A variety of ribosomal inhibiting or inactivating proteins (RIPs) are known in the art, including ricin, momorcharins, and trichokirin, and trichosanthin. These are more fully described in U.S. Pat. Nos. 4,795,739 and 4,869,903, which are hereby incorporated by reference. Of particular interest with respect to the present invention are trichokirin and trichosanthin. RIPs are effective in a dose ranging from about 5 μg/kg/dose to about 100 μg/kg/dose, more particularly from about 10 μg/kg/dose to about 80 μg/kg/dose, and, with respect to trichosanthin, from about 10 μg/kg/dose to about 25 μg/kg/dose. Higher doses of trichosanthin may be efficacious and are fully anticipated according to the present invention. RIPs are generally administered in parenteral formulations.

According to the subject invention, efficacy of treatment is measured in terms of host CD4+ cell number, with a stabilization of CD4+ cell number or increase in cell number following treatment as compared to pretreatment is defined as an efficacious result.

Although there are few studies in the literature concerning the effect of combination anti-viral therapy, the natural history of the disease is known from examination of the placebo arms of treatment studies. Thus, by comparison, the placebo arm of the study in which patients were randomized to placebo or two doses of zidovudine showed a decrease of 16 cells/year. Fischl, M. A., et al., *New Engl. J. Med.* (1987)317:185–91. This is far less than the rate of loss in the patients in this study, prior to receiving trichosanthin, and confirms that they met the entry criteria of the study and were failing AZT. In that same study, the group treated with 500 mg of zidovudine, which proved to be the best treatment regimen, gained 39 cells/year. The patients in that study were quite different from those in this study, since those in the study reported here, having failed AZT, were substantially further along in their disease course. However the addition of trichosanthin reversed this trend to a magnitude substantially greater than that seen in patients receiving zidovudine as first line therapy. Overall, 46 of the 69 patients either decreased the loss of CD4+ cells or showed an increase when trichosanthin therapy was added to the treatment regimen. Prior to trichosanthin, on anti-virals alone, patients were losing CD4+ cells at a rate of 0.91 cells/week, or 47 cells/year. After trichosanthin therapy was instituted, there was an average gain of CD4+ cells of 1.71 cells/week, or 89 cells/year. This is both a surprising and unexpected result since trichosanthin alone, at the dose range employed in this study, is apparently ineffective in improving CD4+ cell counts in HIV infected hosts.

The following examples are offered by way of illustration and not limitation.

EXPERIMENTAL

Materials and Methods

I. Trichosanthin

Clinical grade trichosanthin was obtained from the Shanghai Institute of Organic Chemistry, Shanghai, China, provided as a crystalline product dissolved in sterile distilled water, in ampulses containing 1 ml of solution at a concentration of 1.2 mg/ml. The five lots used in the clinical studies were tested by SDS-PAGE and isoelectric focusing which demonstrated a pure protein product of characteristic molecular weight and isoelectric point. Each lot was tested for its ability to specifically eliminate mononuclear cells that express HIV antigens on their cell surface, and all lots were similar. McGrath, M. S., et al., *Proc. Natl. Acad. Sci. USA* (1989)86:2844–48. The appropriate amount of trichosanthin was diluted into 500 ml of 5% dextrose in sterile water just prior to administration.

II. Clinical protocol

This was a single institution phase II outpatient study. Patients were between the ages of 18 and 65, diagnosed with HIV disease by positive serology, who had been receiving either zidovudine at the optimal dose (300–500 mg/day), or ddI, for at least 1 year prior to therapy, and had failed these drugs as manifest by failure to stabilize CD4+ values, by CD4+ cell levels decreasing by 50 cells/$mm^3$/year, or by significant decreases in CD4+ cell levels on two sequential measurements just prior to therapy. Trichosanthin was administered intravenously (IV) at a dose of one ampule/week (1.2 mg/dose or a range of about 13 μg/kg/dose to 17 μg/kg/dose, depending upon the body weight of the patient), once a week for two weeks, then monthly, infused over a period of two hours. The exception to this were 11 patients entering the study with CD4+ cells less than 50 cells/$mm^3$, who received 0.4 mg as the first dose, than 0.8 mg, than full dose of 1.2 mg from then on, as well as the first group of 23 patients who entered the study. Before the first infusion, two test doses of 0.5 μg and 5 μg each in 1 ml of 5% dextrose in water were administered as an IV bolus, with observation for 30 minutes between each test dose.

All patients remained on the same dose of AZT or ddi during the study period as they were taking prior to the study. All patients with CD4+ cells less than 200/$mm^3$ were receiving aerosolized pentamidine 300 mg/month; some patients with CD4+ cells between 200 and 300/$mm^3$ also received aerosolized pentamidine therapy. Those patients who had an episode of herpes simplex were receiving acyclovir, 600 mg/day, and remained on this therapy through the study period. Some patients were receiving transfer factor, prepared as previously described (Levin, A. S., et al., *J. Clin. Invest.* (1975)55:487–99), administered intramuscularly every two weeks, prior to the study as prophylaxis against viral infections. In almost all cases this was discontinued during the study period. Some patients received dextran sulfate 1800 mg/day during the pre-study period and in all cases this was discontinued at least 4 months prior to entry into the study.

To enter the study, patients must have had between 50 and 500 CD4+ cells/$mm^3$, and be positive for HIV infection by serology. They must have had granulocytes greater than 1000/$mm^3$, platelets greater than 100,000/$mm^3$, hemoglobin greater than 8.5 mg/ml, with bilirubin less than 1.5 times normal, aspartate lysine transaminase and aspartate serine transaminase less than 3 times normal, and creatinine less than 1.5 mg/dl. Pregnant or breast feeding women or those not practicing birth control were excluded from entry.

Prior to entering the study patients signed an informed consent, their medical history was taken, and a physical exam, Karnofsky score, 12 lead EKG, and chest X-Ray were performed. Additionally, normal magnetic resonance imaging or computerized tomography of the brain, or neuropsychiatric testing were required prior to entry. Laboratory tests included a complete blood count, urinalysis, serum chemistry panel, erythrocyte sedimentation rate, beta 2 microglobulin, p24 antigen and antibody levels, all within 2 weeks of the initial trichosanthin administration. Physical examination was repeated every 2-4 weeks, and laboratory values at least once every 2 months.

Trichosanthin was administered on an outpatient basis. Physicians were in attendance during administration, with vital signs recorded every 30 minutes. Following treatment, patients were then discharged into the care of a medically trained person, or informed layman, who performed mental status tests every 4 hours for the next 60 hours. Those patients with suspected mental status change occurring during this time were given dexamethasone, 8 mg IV, every 4 hours until symptoms resolved, usually following hospital admission.

When allergic reactions occurred during therapy, patients were treated with benedryl, 25 mg IV push, and dexamethasone, 8 mg IV, and the infusion was continued after resolution of all symptoms (usually 15 minutes) with no further problems; for subsequent infusions, such patients were premedicated with oral benedryl and dexamethasone the night before infusion then every 4-8 hours until the morning after the next infusion.

III. Serum HIV p24

HIV p24 antigen was determined using a Coulter p24 antigen capture ELISA assay. Byers, V. S., et al., *AIDS* (1990)4:1189-96. Serum p24 antigen is captured by anti-p24 monoclonal antibody and detected by labelled polyclonal anti-p24 antibody. The detection limit of the assay is 7-10 pg/ml and test to test variation is about 15%.

IV. Lymphocyte analysis

Peripheral blood was reacted with fluorochrome labelled monoclonal antibodies Leu 2, 3, or 4, (Becton-Dickinson, Mt. View, Calif.), and following lysis of red cells the leukocytes were analyzed by two color flow cytometry within 24 hours of collection.

V. Patient populations

One hundred twelve patients were analyzed for safety, meeting the criteria of receiving at least one infusion of trichosanthin, and being evaluable for 7 days afterwards. Of these, 16 patients failed one of the entry criteria, having less than 50 CD4+ cells; these patients were analyzed for safety but not efficacy.

Patients were followed for seven days after the last infusion and any new abnormalities found on physical examination or elevations greater than 2 fold on laboratory parameters from baseline and above the normal range were recorded.

Patients were evaluated for efficacy by examining change in the CD4+ cell levels before and after initiation of trichosanthin therapy. Many patients had CD4+ levels evaluated for 1-3 years, while receiving AZT, prior to initiation of trichosanthin therapy. Most patients were followed for about 6 months after initiation of experimental therapy. Therefore, the time on AZT alone was matched with the time on AZT and trichosanthin for each patient, and CD4+ levels were considered during these times. For example, if a patient received AZT with trichosanthin for 5 months, the CD4+ cell levels during this time were compared with the levels for only 5 months prior to initiation of trichosanthin therapy, even though longer pretreatment times were available. Only patients with at least 2 pretreatment CD4+ values in addition to baseline were evaluated. Because of fluctuation in the CD4+ cell levels, it was not possible to fit a statistically significant line to the CD4+ level data points. Therefore, the changes pre- and post-trichosanthin were determined by measuring the area under the curve (AUC) for each patient. This allowed measurement of the change of CD4+ cell levels on a weekly basis. The two values, pre- and post-trichosanthin, were compared for each patient using a paired Student's T test.

Sixty-eight patients had at least two CD4+ evaluations pre- and post-trichosanthin treatment. These patients were analyzed by determination of the area under the curve defined by the CD4+ cell levels, and this provided CD4+ mean values before and after trichosanthin treatment.

VI. Statistical Analysis

A time averaged mean CD4+ cell change relative to baseline (CD4+ mean) was determined. This parameter was calculated as the area under the CD4+ cell concentration curve from either day 0 or the most proximal CD4+ determination prior to start of therapy to the final available determination after subtraction of the baseline value from all subsequent measurements. This area was then divided by the period of observation (days) to give a CD4+ mean (cells/mm$^3$). In each patient a CD4+ mean value was calculated by analysis of CD4+ levels for a comparable period before trichosanthin treatment. These periods of time varied with respect to individual patients, and data are presented as CD4+ cells/week.

EXPERIMENTAL STUDIES

Example I

I. Study Patients

One hundred twelve patients were treated on this protocol. One hundred five were failing zidovudine at doses of 300-500 mg/day but remained on this drug during therapy; 7 were failing ddi at a dose of 250 mg b.i.d. and also remained on this drug during trichosanthin therapy. All patients were treated with at least one dose of trichosanthin and received follow-up care for at least 7 days. These patients are included in the safety analysis. Sixty-eight patients had at least two pre-treatment CD4+ cell levels measured (R1), and at least two values after trichosanthin therapy (R2), these patients were evaluated for efficacy by comparing their R1 and R2 values. An additional 7 patients had at least two values of CD4+ cells after trichosanthin treatment, but lacked CD4+ determinations pre-trichosanthin.

The majority of patients were male homosexual caucasians. Their age and weight was quite homogenous, allowing standard treatment with a set dose (1.2 mg). This produced a range of about 11.2 to 25.5 µg/kg/dose. The majority of patients were asymptomatic although 34 had prior illnesses defining them as having AIDS Related Complex (ARC), and 16 were classified as patients with Acquired Immune Deficiency Syndrome (AIDS). Patients received monthly infusions of trichosanthin and those who exited the study prior to completion did so for reasons other than toxicity. Upon completion of the study, 37 patients had their last infusion within 60 days and an additional 37 had the last infusion within 90 days. The mean CD4+ levels at the start of trichosanthin were just over 200 cells/mm$^3$. Thirty patients entered the study with CD4+ values less than 100 cells/mm$^3$ and were pre-treated with dexamethasone prior to the start of trichosanthin; these patients received initial doses of 0.4 mg/dose, with dose escalation to full dose on later infusions. Most patients had CNS evaluation prior to entering the study, and all were negative except for two patients who had a past history of AIDS related dementia and showed atrophy on MRI but no evidence of HIV encephalopathy by either MRI or clinical examination. There was no significant difference between the demographics of the total number of patients treated and evaluated for safety, and those evaluated for efficacy.

II. Concomitant Medications

Patients were on the optimal dose of zidovudine, ranging from 300-500 mg/day; over the period prior to trichosanthin treatment some patients had dropped from 500 to 300 mg/day but all remained on the same dose of zidovudine during trichosanthin treatment as they were receiving in the 60 days prior to treatment. Six patients had progressed to ddI prior to trichosanthin therapy either because zidovudine was too toxic, or because of continuing decrease in CD4+ cell counts. These patients continued to suffer declines in CD4+ cells despite the optimal dose of ddI for at least 60 days. Most patients received 4-6 doses of trichosanthin; the average number was 4.9. Forty-nine patients received acyclovir because of previous herpes simplex infection; all remained on this therapy during trichosanthin infusions. All patients whose CD4+ cell counts were >200/mm$^3$ were receiving aerosolized pentamidine monthly as prophylaxis against pneumocystis and continued this therapy during trichosanthin treatment. In contrast, most patients receiving either transfer factor or dextran sulfate prior to trichosanthin stopped these drugs during the trichosanthin infusions.

III. Side Effects

The 112 patients evaluated for side effects of trichosanthin received a total of 526 infusions. They were evaluated for any laboratory or clinical abnormalities during the weekly or monthly infusions or within 7 days after the last infusion. All patients developed myalgias and arthralgias primarily of the upper trunk, hands and arms, with myalgia extending up into the neck. In all cases this was moderate in intensity, appearing within 36 hours of infusion and lasted for 2-3 days. Symptoms were treated with nonsteroidal anti-inflammatory agents; hospitalization was not required. No patient developed hypoalbuminemia, which is often noted at higher doses of trichosanthin. All patients developed fever 36-60 hours after the first infusion. These were mild to moderate in intensity; the highest level was 39.5° C. Both the fevers and myalgias tended to decrease by the time of the third and subsequent infusions. Apart from this, the principal changes during therapy were in the liver function tests, and usually occurred in patients entering the study with abnormally elevated values. Ten to 13 patients had a 3 fold increase or greater in the SGOT and SGPT. This increase occurred 68 days after the first infusion following an average of 3 infusions, and returned to baseline in all cases even though trichosanthin infusions were continued for an average of two additional infusions. An average of 47-51 days were required for the values to return to baseline. In one of these cases there was an elevation of the total bilirubin, which also returned to baseline during subsequent trichosanthin infusions. This patient was documented to have developed hepatitis A while on therapy. Similarly, 2 and 4 patients experienced a transient thrombocytopenia or anemia during infusions; these were mild, and reversible. Twenty-four patients developed anaphylactoid reactions during therapy. On the average among these 24 patients, the anaphylactoid reaction developed after the 4th infusion and presented as erythroderma, periorbital edema, and occasional upper airway wheezing without abnormalities in the lower airway. In most cases, benedryl administration allowed completion of the infusion. These patients were pre-treated with dexamethasone prior to any subsequent infusions which were well tolerated.

Mental status changes were only seen in 2 of the 7 patients receiving ddI as their concomitant anti-viral. One patient developed a mild syncopal episode during the first infusion, and received 3 subsequent infusions without incident. Another patient developed a grand mal seizure 36 hours after the first infusion. He received 6 subsequent infusions without incident. In both cases, however, the patients were removed from ddI and re-started on zidovudine prior to additional trichosanthin infusions.

Three deaths occurred in this group of patients. One patient had Kaposi's Sarcoma, and had received multiple transfusions because of zidovudine toxicity, resulting in hemolytic anemia. This death, of hemolytic anemia, occurred 50 days after the last infusion. A second patient died of pneumocystis pneumonia 187 days after the last infusion. A third patient, a heavy smoker, died of bronchogenic carcinoma 180 days after the last infusion. Retrospective analysis of the chest X-ray taken at study entry indicated the presence of carcinoma at the start of the study.

IV. Changes in CD4+ cell counts as a measure of treatment efficacy

All patients were characterized as having failed AZT, although 21 patients had a net stabilization or increase in CD4+ cells when assessed over the entire pre-treatment period. The average length of pre-treatment follow-up, on AZT but prior to receiving trichosanthin was 197+/−86 days. When the rate of change in CD4+ cell levels was assessed by AUC analysis, over the period of time analyzed, patients had lost an average of 0.91 cells/week pre-treatment. The average length of follow-up of patients receiving AZT with trichosanthin was 165+/−58 days. During that time the average gain of CD4+ cell numbers was 1.71 cells/week. Comparison of these two values by paired sample Student's T test indicated a significant response to trichosanthin treatment ($p=0.005$) This was also supported by analysis by the Wilcoxon matched pairs signed rank test (p less than 0.0001).

Overall, 40 patients either stabilized their levels of CD4+ cells, or gained cells, and an additional 10 decreased the rate of loss during therapy with trichosanthin. If the rate of change in CD4+ cells during therapy with AZT alone is compared to the rate of change when trichosanthin was added to the treatment regimen, there was an average change of +0.58 cells/day. In the 75th percentile the change was +2.73 cells/day (R2-R1). To determine if the response could be predicted, patients were ranked as to their relative change in loss or net gain of CD4+ cell levels before and after trichosanthin treatment. This was compared with the CD4+ levels, CD8+ cell levels, beta 2 microglobulin levels, erythrocyte sedimentation rate, and anti-p24 antibody titers at the start of trichosanthin treatment. Only the CD8+ cell levels were significantly associated with response.

V. Serum p24 antigen levels

Twenty-one patients entered the study with elevated levels of p24 antigen, and two patients converted from positive to negative. An additional 3 patients who were p24 antigen negative at study entry converted during treatment with trichosanthin. An additional 6 patients transiently converted to positive during therapy with trichosanthin but were negative at study end. Overall there was no significant difference between the pre and post treatment levels of p24 antigen. However, more patients increased their antigen level by at least 50% at study exit (as compared to their pre-treatment values), than remained stable or decreased the level by at least 50%. Clinically, there was little change in disease related status, with all patients who entered the study asymptomatic (51) remaining that way at conclusion of study, and 13 entering trichosanthin therapy with an AIDS diagnosis remaining in that category. However of the 32 patients with a diagnosis of ARC at start of trichosanthin therapy, 2 converted to AIDS during the therapy with trichosanthin. One developed MAI, and a second developed pneumocystis pneumonia.

It will be apparent to those of skill in the art that the present invention adds to the state of the art novel methods for the treatment of retroviral infections, particularly HIV disease, that are more efficacious than prior known methods. Increased efficacy is attained by the administration of a ribosomal inhibiting protein, such as trichosanthin, in combination with a an anti-retroviral agent, such as zidovudine.

Although the present invention has been described in some detail for the purposes of clarity and understanding, it will be obvious to those skilled in the art that certain changes and modifications may be practiced within the scope of the appended claims.

What is claimed is:

1. A method for increasing the number of CD4+ T cells in a host having a retroviral infection and failing anti-retroviral therapy as measured by CD4+ T cell number comprising administering to the host an anti-retroviral agent and a ribosomal inhibiting protein.

2. The method according to claim 1, wherein the host is a human.

3. The method according to claim 1, wherein the retroviral infection is human immunodeficiency virus infection.

4. The method according to claim 1, wherein the anti-retroviral agent is a reverse transcriptase inhibitor.

5. The method according to claim 4, wherein the reverse transcriptase inhibitor is zidovudine.

6. The method according to claim 5, wherein the dose of zidovudine is between about 300/mg/day to about 500/mg/day.

7. The method according to claim 1, wherein the ribosomal inhibiting protein is trichosanthin.

8. The method according to claim 7, wherein the dose of trichosanthin is between about 10 μg/kg to about 100 μg/kg.

9. The method according to claim 8, wherein the dose of trichosanthin is between about 10 μg/kg and about 25 μg/kg.

* * * * *